United States Patent [19]

Kwiat et al.

[11] Patent Number: 4,652,811
[45] Date of Patent: Mar. 24, 1987

[54] METHOD FOR MEASURING LIQUID CONTENT IN A POROUS MEDIUM SUCH AS SOIL

[75] Inventors: Doron Kwiat, Tel Aviv; Dov Ingman, Haifa, both of Israel

[73] Assignee: K.I.T. (MEDIDOT) Ltd., Haifa, Israel

[21] Appl. No.: 606,607

[22] Filed: May 3, 1984

[30] Foreign Application Priority Data

May 3, 1983 [IL] Israel .................................. 68549

[51] Int. Cl.$^4$ ......................... G01V 3/06; G01R 27/02
[52] U.S. Cl. .............................. 324/65 R; 324/61 R; 324/65 P; 73/304 R
[58] Field of Search ................ 73/73, 336.5, 304 R, 73/304 C; 200/61.04, 61.05, 61.06; 340/618, 602, 620; 324/355, 357, 65 R, 65 P, 61 R

[56] References Cited

U.S. PATENT DOCUMENTS

| | | | |
|---|---|---|---|
| 3,553,577 | 1/1971 | Stromberg | 324/65 R |
| 3,631,337 | 12/1971 | Mackinney | 324/65 R |
| 3,680,028 | 7/1972 | Black | 324/65 R |
| 3,807,055 | 4/1974 | Kraxberger | 73/336.5 |
| 3,945,217 | 3/1976 | Bashark | 73/336.5 |
| 3,961,753 | 6/1976 | Sears | 324/65 R |
| 3,982,177 | 9/1976 | Walker | 324/376 |
| 4,281,289 | 7/1981 | Donaldson | 324/355 |
| 4,553,087 | 11/1985 | Kühn | 73/73 |

FOREIGN PATENT DOCUMENTS

| | | | |
|---|---|---|---|
| 2147490 | 3/1973 | Fed. Rep. of Germany | 324/65 R |
| 813921 | 11/1936 | France | 73/304 |
| 1052968 | 11/1983 | U.S.S.R. | 324/65 R |

Primary Examiner—Reinhard J. Eisenzopf
Assistant Examiner—Jose M. Solis
Attorney, Agent, or Firm—Dennison, Meserole, Pollack & Scheiner

[57] ABSTRACT

A method for measuring liquid content of a porous medium such as soil applies a voltage to a plurality of point contacts placed in the porous medium to be measured for liquid content, as well as to a common electrode also inserted into the porous medium to be measured in spaced relation to the point contacts. Liquid content in the soil is determined as a function of the number of the point contacts having electrical continuity with the common electrode through the porous medium to be measured for liquid content. A predetermined electrical resistance is inserted between each of the point contacts and a source of the voltage applied to the point contacts.

5 Claims, 12 Drawing Figures

METHOD FOR MEASURING LIQUID CONTENT IN A POROUS MEDIUM SUCH AS SOIL

This invention relates to methods and means of measurement, specifically the nondestructive measurement of the liquid content (such as water) or the salinity of porous media (such as soil). It is based on the measurement of two physical parameters one of which is dependent exclusively on the moisture content of the porous medium while the second is dependent on the combination of both the liquid content (i.e. water) and the salinity.

The invention is intended for real-time measurement of liquid content in porous media (water in soil). The measurement may be made on a single-point basis or in a three-dimensional way at a number of arbitrary points simultaneously.

Another purpose of this invention is control of the liquid contents in porous media, (moisture in soil) and also the salinity of the solution in the porous media, (the percentage of fertilizer in the soil solution). It may be used also for controlling industrial processes (for example the percentage of moisture in coal dust fed to coal-fired power plants)

The device is composed of a display and a probe. The probe is brought into contact with the porous medium by, for example, inserting it into the soil. The probe enables obtaining information about the liquid content of the porous medium or information concerning the salinity of the medium in its vicinity. This measurement of liquid content in the porous medium, and of the salinity of the solution in the porous medium can be obtained from a single probe or from a probe made of two separate units, in which each unit measures one of the parameters.

Dispersing a set of probes in the porous medium enables simultaneous three-dimensional mapping of the moisture content and salinity of the medium and their variation in time and space.

Data may be read from the probes in two ways, either in a separate manner by connecting the probes one by one to a single display and reading the results separately, or in a centralized manner by connecting all probes to a single central display.

The connection to the display can be made either by direct electrical connection or by radio transmission or other means of data transfer. The display enables reading of liquid content or salinity of the medium in the vicinity of the probes.

The display can be an integral part of an automatic control system designed for monitoring liquid content in porous media (for example control system for irrigation) or control system for coal moisture in a power plant). The probe enables receiving information on the moisture at various depths along the length of the probe and at the same time from a number of points. A group of probes dispensed in the medium enables receiving simultaneously a three dimensional map of the medium's moisture content and the changes of this moisture content both in space and time.

Two method and systems for measuring moisture substantially independent of salinity are disclosed. In one, salinity remains a factor, but the effect thereof is substantially reduced from that evidenced by straight conductivity. In the other, salinity is substantially eliminated entirely as a factor, comparison of either measurement with soil conductivity enables salinity to be determined.

One of the instruments and methods described below enable measuring of a physical parameter dependent on the combination of the moisture content and salinity of the porous media, the parameter being based on measuring electrical resistance, or the electrical current between flat, linear, single-point or area-covering electrodes. The salinity unit of FIG. 7 comprises a conductivity device including a series connected A.C. voltage source $1'$, ammeter $2'$ and data translater $3'$ series connected with a pair of spaced apart electrodes $4'$.

The other instrument and the methods described below enable measurement of a physical parameter dependent exclusively on the liquid content of the porous medium. Measuring the two parameters enables, therefore, independent determination of the characteristics of the liquid content and of the salinity of the solution in the medium.

There exist instruments and methods for electrical measurement of moisture content. Damp mediums, such as soils, are electrolytic and are characterized mainly by a number of electrical parameters such as: electrical conductivity, electrical capacitance and inductance. These parameters vary with the characteristics of the medium. The main characteristics which influence these parameters are the medium's density, structural form, chemical composition (particularly salinity) and moisture content.

The instruments and measuring means which operate on electrical principles may be classified into two major catagories, those based on a direct current source and those based on an alternating current source. The invention described in U.S. Pat. No. 3,882,383 can be cited as an example of a measuring instrument which measures electrical conductivity of soil using a d-c source.

The deficiencies of the invention disclosed in this Patent are as follows:
  (a) strong influence of the soil's unstable polarization voltage.
  (b) strong influences of variations in soil salinity on the electrical conductivity.
  (c) the form of moisture distribution between the electrodes influences the conductivity as a result of spatial asymmetry in the electrical field.

The invention described in U.S. Pat. No. 3,870,951 is another example of a moisture measuring instrument whose voltage measurements utilize a high-frequency a-c source. The weak points of the invention described in this Patent are as follows:
  (a) sensitivity of readings to the variations in inductance and capacitance which result from variations in the acidity level (pH).
  (b) influence on the readings of skin effect by use of high frequency (RF)

There exist, also, methods based on measurement of electrical conductivity in clays or other water-absorbing materials which are in moisture equilibrium with the medium being tested. The major deficiences in the latter types of methods and instruments are:
  (a) Hysteresis in measured results.
  (b) long reaction times which do not allow reading of rapid moisture variations.
  (c) Formation of salt layers around the absorbing material which change the readings.
  (d) Dissolution of the clay or absorbing material.

The instrument and the method described below enable measurement of a physical parameter dependent exclusively on the liquid content of the porous medium and also for measuring of a physical parameter dependent on the combination of the moisture content and salinity of the porous media, the parameter being based on measuring electrical resistance, or the electrical current between flat, linear, single-point or area-covering electrodes. Measuring the two parameters ebables, therefore, independent determination of the characteristics of the liquid content and of the salinity of the solution in the medium.

The objects of the invention presented by us are the following:
(a) separating of effects of salinity from the effects of moisture content on the measurements.
(b) reduction of the influence of the capacitance and the inductance of the medium on the readings.
(c) neutralization of the effect of polarization on the measurements.
(d) prevention of hysteresis in readings (high degree of reproducibility).
(e) obtaining a very rapid reaction in readings upon change in moisture content.
(f) obtaining a very rapid reaction in readings upon changes in salinity.

Objective (a) is obtained as mentioned above by separate measurement of the two physical parameters, one dependent on the effects of liquid content and salt, and the other dependent exclusively on liquid content in the medium. Proper combination of the reading from the two measurements provides the needed separation.

DESCRIPTION OF THE DRAWINGS

FIG. 5 is a diagrammatic illustration of the interaction of multiple moisture droplets in a porous medium on a plurality of spaced apart point contacts; electrical, optical, or the like;

DETAILED DESCRIPTION OF THE INVENTION

Let us first examine the following case consisting of two electrodes 1 and 2 (FIG. 1) whose outer surfaces along are in contact with the conducting medium, and which are provided with electric potentials $\phi_1$ and $\phi_2$. In the medium between the electrodes the following equations apply:

$$\int_s \vec{J} \cdot \vec{d_s} = 0 \text{ for each closed area element (see FIG. 1)}$$

$$\int_s \vec{J} \cdot \vec{d_s} = \int_v \vec{\nabla} \cdot \vec{J} d^3v \text{ Gauss Law}$$

From these one obtains:

$$\vec{\nabla}\vec{J}=0$$

Figure 1:
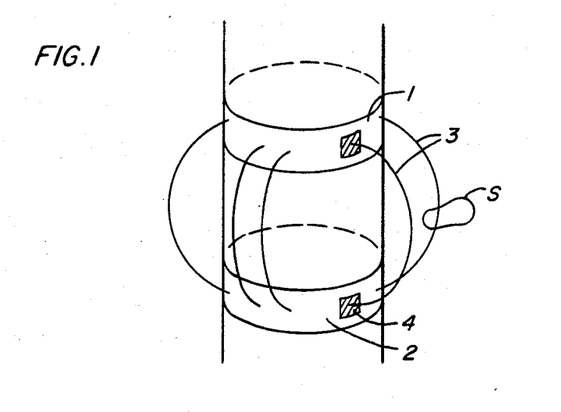
FIG. 1 is a diagrammatic illustration of a probe carrying a pair of spaced apart ring electrodes energized to provide an electric field therebetween.

In a conductive medium the following is known to apply: $\vec{J}=\sigma\vec{E}=-\sigma\vec{\nabla}\phi$ Assuming a homogeneous medium between the electrodes, i.e. 94=const. one obtains: $\nabla^2\phi=0$ with the following boundary conditions:
$\phi=\phi_1$ on the surface of electrode 1. and
$\phi=\phi_2$ on the surface of electrode 2.
The current of the electrodes are given by:

$$I = \int_s \vec{J} \cdot \vec{d_s} \text{ where the integral is taken over the electrode ring.}$$

Owing to the fact that the electrodes are equipotential, the field and thus also the current is perpendicular to the electrodes surface, one obtains, therefore:

$$I = \int_s J \cdot ds = \sigma \int_s E ds$$

This equation holds true only when the entire surface of the electrodes is in electrical contact with the conducting medium. The electrical field in the medium is determined by the potential difference between the two electrodes and the geometry of the probe and is not dependent on the nature of the contact between the electrodes and the medium. The current itself must flow along the field lines with the assumption of a homogeneous and conductive medium, a required and sufficient condition for current passage between a point on the surface of one electrode (4) to a point on the surface of the other electrode along a certain field line (3) is the existence of conductive contact between the electrodes and the medium at both points simultaneously.

Only field lines meeting this condition contribute to current flow between the electrodes.

The current flow between the rings, therefore, is given by:

$$I = P_1 \cdot P_2 \cdot \sigma \int_{s \text{ electrodes}} E \cdot d_s$$

wherein $P_1$ is the probability of the existence of conductive contact at the point between electrode 1 and the medium, and $P_2$ is the probability between electrode 2 and the medium.

In a homogeneous medium, the probabilities $P_1$ and $P_2$ are equal and are given by:

$$P_1 = P_2 = P = \frac{\text{contact surface}}{\text{electrode surface}} = \frac{S \text{ contact}}{S \text{ electrode}}$$

In a damp medium, the electrical contact area is that area of the electrode surface which comes in contact with water. Obvously this area is given by:

$$S \text{ contact} = W^{\frac{2}{3}} S \text{ electrode}$$

where W is the moisture volume to total volume factor. The current obtained is given, therefore, by $$I = \frac{S_{contact}^2}{S_{electrode}^2} \cdot \sigma(W) \cdot \int_{S \text{ electrode}} E d_s$$

Since the electric field is not dependent on the quality of contact but only on the geometry and the potential difference, the integral is a constant value for fixed conditions of geometry and potential difference.

Let us designate:

$$A_{s1E} = \int_{s \text{ electrode}} E \cdot d_s$$

we can then write $$I = \frac{S^2 \text{ contact}}{S^2 \text{ electrode}} \cdot \sigma(W) A_{s1E}$$

Using the equation mentioned above $$S_{contact} = W^{\frac{2}{3}} S_{electrode},$$

we obtain the following relationship:

$$I = A_{s1E} E \sigma(W) \, W^{4/3}.$$

From the literature, it is known that $$\sigma(W) = \sigma_o \frac{(1-a)W}{1-aW}$$

where $\sigma_o$ stands for water conductivity (only in the medium) and a is a characterizing parameter for the medium itself.

This equation assumes zero electrical conductivity in a dry medium. The above equation can be approximated in the form:

$$\sigma(W) = \sigma_o C W^\alpha$$

where $\alpha$ is the influence of the conductivity factor along (without the area contact effect). It's value will generally be $1.2 < \alpha < 1.5$.

Finally, by substitution, the following relationship is obtained:

$$I = C \sigma_o A_{s1e} W^{(4/3+\alpha)}$$

Letting $\gamma = 4/3 + \alpha$ the equation can be rewritten as $$I = C \sigma_o A_{s1E} W^\gamma$$

For an average value of $\alpha$ of 1.33 we found that $\alpha/\gamma \alpha 0.5$.

The effect of variations in conductivity on the measured current is one half of the influence of moisture on the overall current (conductivity plus contact area).

Measurement of moisture in the medium, as proposed in this invention, is, therefore:

$$W = \left[ \frac{I}{C \sigma_o A_{s1E}} \right]^{1/\gamma}$$

(where I is the measured current).

While moisture measurement by a method based on conductivity is:

$$W = \left[ \frac{\sigma_{measured}}{C \sigma_o} \right]^{1/\alpha}$$

The relative errors caused by variations in $\sigma_o$ due to salinity variations in the two methods is as follows:

The error for the disclosed invention is $$(\Delta W/W)_{KIT} = \frac{1}{\gamma} \Delta \sigma_o / \sigma_o$$

The error for the method based on conductivity alone is:

$$(\Delta W/W)_{COND} \approx 1/\alpha \, \Delta \sigma_o / \sigma_o$$

Thus, it is clear that the effect of change in salinity on the results is smaller by the new method proposed by us compared to its effect on the other method based on conductivity measurement by a factor of $\alpha/\gamma \approx 0.5$.

To overcome the problems resulting from unstable voltage in the electrolytic medium (polarization, etc.) the following actions are taken in accordance with this invention:

(a) The polarity of the voltage between the electrodes and the polarity of the d-c ammeter are switched simultaneously by an electronic circuit.

(b) The rate of polarity switching between the electrodes, and the polarity in the ammeter, is selected in accordance with the following considerations:

(1) The period, T, of polarity switching is much greater than the electrical relaxation time of the medium (medium) $\tau_{med}$.

(2) The time constant of the d-c, meter, $\tau_{meter}$, is much greater than the period T.

That is to day, the selection is made so that we maintain the condition:

$$\tau_{medium} << T << \tau_{meter}$$

note: The polarization voltage in the medium is unstable but the varitions are slow with respect to the above values.

Figure 2:
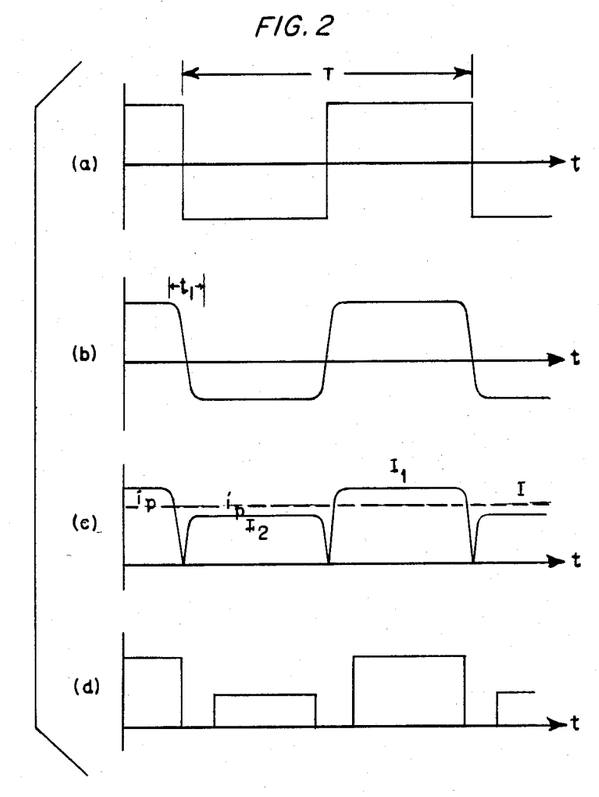
FIG. 2 is a diagram illustrating a number of waveforms demonstrating the effects of switching potential polarities on the electrodes of FIG. 1.

The waveforms in FIG. 2 illustrate the following processes:

(a) The switching of polarity at a period T (b) The behaviour of the current between the electrodes, (asymmetrical owing to the polarization existing in the medium) showing the reaction time $t_1$ caused by the time constant of the medium.

The order of magnitude of $t_1$ is approximately that of $\tau_{medium}$ ($t_1 \sim 3\tau_{medium}$).

(c) Current through the d-c ammeter as a result of the synchronized switching of the current and the ammeter connections and the average current as measured by the ammeter whose time constant is much larger than the period T.

The average current I is the current which would have been obtained if the polarization current $i_p$ did not exist in the medium. The value I is defined by $I_1 = I + ip$, and appears in the medium when the polarization current is in the direction of current I. $I_2$ given by $I_2 = I - ip$, exists in the medium when the polarization current opposes current I.

(d) Approximation of the current in the medium used for estimating the error.

FIGS. 2c and 2d show that the average current in Figure c is greater than the average current in Figure d. In general average current is given by:

$$\frac{1}{T} \int_0^T i(t)dt.$$

The average current of Figure d is given therefore by:

$$\frac{1}{T} \{I_2(T/2 - t_1) + I_1(T/2 - t_1)\}$$

From the expressions for $I_1$ and $I_2$ we find that the approximate average current in Figure d is:

$$I(1 - 2t_1/\tau)$$

The maximum error is therefore $2t_1/T$ (relative error of the measured current).

Since $t_1$ includes the influences of the time constants introduced by capacitance and inductance etc., and it is much smaller than T, the maximum relative current error from the above causes is negligible.

In conclusion the novelty of this aspect of invention may be defined as follows:

(a) To minimize the effect of changes in salinity of the medium and the resulting changes in electrical conductivity, a parameter is measured which is directly dependent on the conductivity of the amount of electrode area in contact with the medium.

(b) To minimize the effects of variations in the unstable polarizing voltage, the measurement mentioned in (a) is combined with a synchronized switch in polarity of the electrodes and the d-c ammeter.

(c) To minimize the effect of capacitance and inductance in the medium, the period T of polarity change is selected, so that:

$$\tau_{medium} << T << \tau_{meter}$$

i.e. the period T is much smaller than $\tau_{meter}$, the d-c ammeter time constant, and is much greater than the $\tau_{medium}$, relaxation time of the medium.

Figure 4:
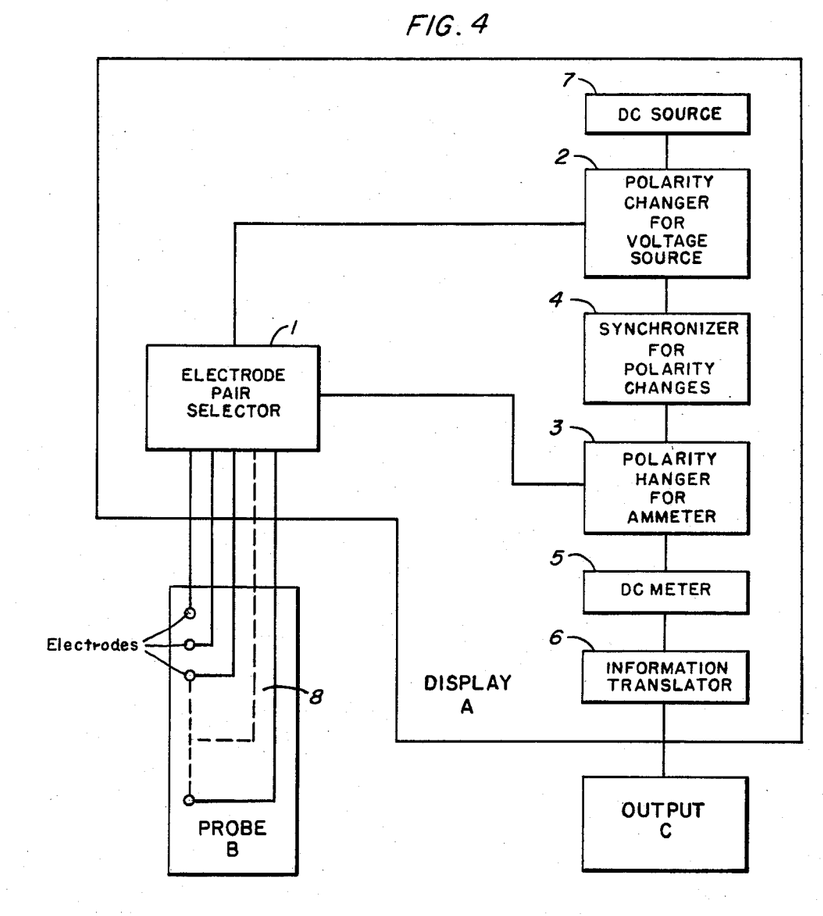
FIG. 4 is a schematic block diagram of an apparatus for moisture measuring in accordance with the present invention.

The following is a description of the apparatus for moisture measuring based on the method and theory described above. The instrument is composed of a display unit and a probe which may be separate units, or combined into a single unit. The probe is a group of electrodes made of conductive material, metal for example, and which are in direct contact with the medium being tested.

The electrodes are electrically connected to the display either by direct permanent connection or by a connector. The probe is shown in FIG. 4 as unit B and includes an arbitrary number of electrodes (8). The display unit, shown as A in FIG. 4, includes the following main sub-units:

(1) A selector of electrode pairs (1) which may be electrical or mechanical switches operated manually or automatically.

(2) A polarity changing switch (2) to switch the voltage source which could be, for example, a rectangular-wave generator, or an automatic electrical switching device operated by an external system.

(3) Ammeter polarity changer (3) such as an automatic switching device operated by outside system or a diode bridge.

(4) Synchronizer for polarity changes (4) which could be, for example, a generator that simultaneously activates automatic switches for the polarity changers (2) and (3) above.

(5) Analog or digital d-c ammeter (5) of suitable time constant.

(6) Electrical output information interpreter, for example, an analog-to-digital translating circuit and microprocessor which performs calculations in accordance with the equations described above in "Theory of the Method".

(7) A direct voltage source (7) such as, for example, a battery.

The unit shown as C in FIG. 4 is the output system and is intended for the instance where there is a need for gathering data and storing it, such as, for the purpose of linking into a computerized irrigation control system.

Following is a description of the apparatus operation:

One inserts the probe into the medium to be measured. During the measurement the probe and the display are electrically connected and the voltage is supplied via the pair selector (1) to a specific pair of electrodes which, because of their position in the medium, represent a certain area for measurements. The voltage applied to these electrodes from voltage source (7) passes through polarity changer (2) and in this manner the voltage on the surface of the electrodes varies with time as shown in FIG. 2a. The current through the ammeter and polarity changer (3) has the form shown in FIG. 2b. Owing to the polarity changing synchronizer (4) we obtain phase synchronization of the polarity changes on the surfaces of the electrodes (8) and on the ammeter (5). We thus obtain the current versus time waveform through ammeter (5) as shown in FIG. 2c. The translation of the electrical information into moisture units is performed by the information translator (6) from which it can be read directly, or transferred to external systems.

The method and the prototype instrument constructed as described above were field tested under varying controlled conditions. (moisture, salinity, densities and varying depths.)

The results of the measurements were compared with the predicted theoretical results of this method and correlated very well.

Figure 3:
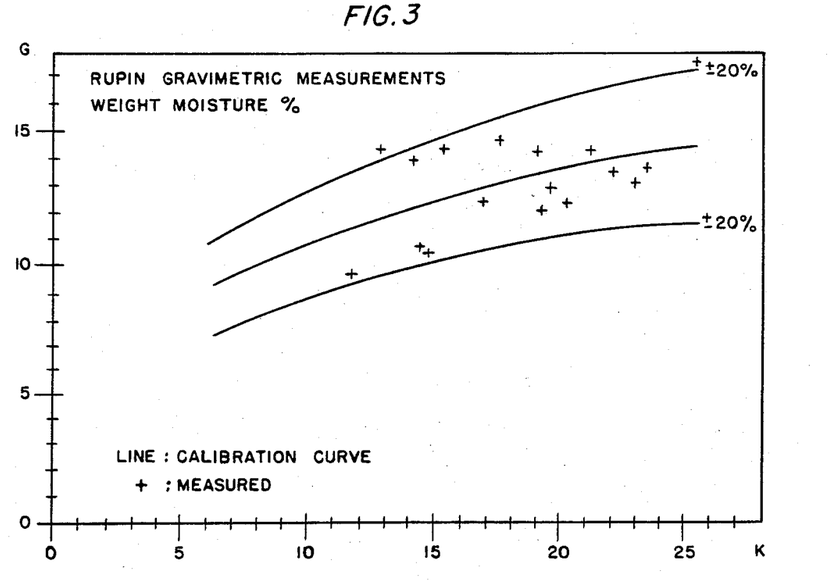
FIG. 3 shows the theoretical curve and the experimental results of application of the present invention to moisture measurements.

FIG. 3 shows the theoretical curve and the experimental results. The deviation between the theoretical and experimental results may be attributed to errors caused by salinity density variations, and also to errors in the base line reference measurements, which were performed by gravimetric methods.

The error in translating the readings of moisture measurements by gravimetric methods is caused by density variations in the medium and is of the order of ±15%. On this basis it is possible to estimate the error of the present method of measuring to be of the order of ±10%, and this holds true for the broad spectrum of densities and salinites of the medium.

All this demonstrates the value of the present invention, the novelty therein and its technical and practical potential.

As pointed out above the method and instruments of the present invention is based on the linking of the separate measurements of two physical parameters. One is dependent exclusively on the moisture content in a porous medium and completely independent of the salinity. The other is affected by both the moisture content of the porous medium and its salinity.

The method and device hereinbefore described provides on approach to measuring liquid content substantially independent of salinity. Other approaches are also possible.

Consider a point probe capable of a discrete reaction to the existence or non-existence of a contact between it and the liquid of the medium. Let P be the probability for the existence of contact between the probe and the liquid and $P_1$ be the probability of the non-existence of this contact. It can be shown that for N point probes, Np is the average number of probes that are in contact with the liquid in the medium.

Because of certain deviations of second order each probe has a probability P slightly different from that of the others. For a large number of points probes (N>>1) these deviations may be considered to cancel each other and thus allow the consideration of an equal probability P for all N probes.

The probability P depends on the effect contact area between the probe surface and all the liquid in the medium, and not on other physical parameters of the liquid.

Figure 5:
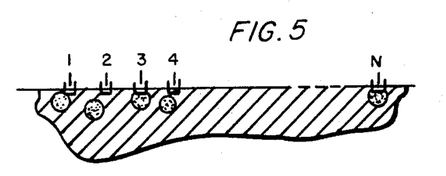

Selecting N>>1 permits assuming identical average surface for all probes. Thus the only parameter affecting P is the effective cross-section of the liquid surface in the point medium which is in contact with the probes (FIG. 5).

It is clear, therefore, that it is possible to write $$P=P(W)$$

that is that the probability P is a function of the liquid content per unit volume symbolized W. To permit independent measurements at each sensor it must be emphasized that the distance between the point sensors should be sufficiently large to prevent contact between them through the liquid. Also, probe structure should not effect liquid distribution in the medium by suction, adhesion or other phenomena. This can be obtained by high surface quality of the probe, and the use of a liquid repelling material.

The average number of sensors in contact with the liquid is $n=NP(W)$ and therefore the average number n of sensors in contact with the liquid is a physical parameter dependent exclusively on liquid quantity in the free volume of the medium, and is independent of liquid characteristics (such as salinity).

The importance of the medium being porous is that porosity allows homogenic distribution of the liquid in the medium. This permits the assumption of medium moisture as an average percentage of liquid in the free volume of the medium and enables us to discuss liquid contact surface with the point sensors.

The second parameter measured is a physical one dependent on the characteristics of moisture content and salinity. A method to measure this parameter was discussed above. The quantity of the liquid in the medium is obtained from the first parameter. Substituting it in the expression for the second parameter enables us to extract the salinity of the liquid as a separate quantity. An example of a physical parameter which depends only on liquid content in the porous medium is the electric current which passes between the group of point sensors and another common electrode. Each point sensor is comprised of a contact with an electrical point conductor, connected to one terminal of a resistor. The resistor is of much higher resistance than the resistance of the measured medium. The other end of the resistor is connected through a series connected ammeter and to a voltage source whose other terminal is connected to the common electrode. Each point conductor is electrically isolated from the other sensors but is in contact with the measured medium (see FIG. 6).

Figure 6:
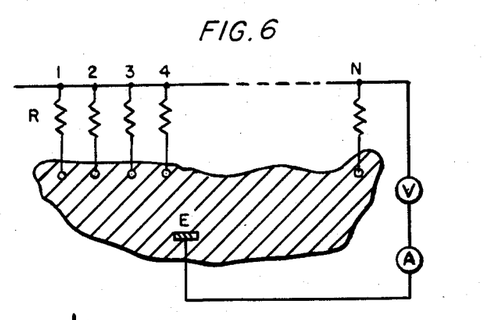
FIG. 6 is a schematic illustration of a device responsive only to liquid content in a porous medium.

As described above in the invention theory, out of the N resistors of the probes, only n resistors are in electrical conductive contact with liquid in the medium wherein $n=Np(W)$. Because the resistance R of each resistor is much higher than the medium resistance, we can say that the resistors which are in electrical contact with the common electrode E (FIG. 6) are connected in parallel. The current flow, therefore, is given by:

$$I = I(W) = \frac{VN}{R} P(W)$$

where V is the voltage of the source and r the resistance of each resistor. It is possible to relate P(W) to the measured medium either by a physical equation or by empirical calibration.

The second physical parameter, that which is dependent on both liquid content and salinity is measured by the method described above and it is the electrical current which is given there by the equation:

$$I = C\sigma_o W^\gamma$$

$\sigma_o$ is dependent exclusively on salt concentration in the solution, and it is possible, therefore, the measure the change in $\tau_o$ due to salinity variation, separately, from moisture variations.

The function P(W) is the probability that the point probe is in contact with the liquid in the porous medium.

This probability is given by:

$$P(W) = \frac{\text{liquid quantity per unit volume of medium}}{\text{total free volume in the medium}}$$

and therefore $P(W)=W/X$
where X is the porosity parameter which expresses the percentage of the volume in a volume unit of the medium.
We find on the one hand that $$I(W) = \frac{VN}{RX} W$$

and on the other hand, $$I(W_1\sigma_o) = C\sigma_o W^\gamma$$

therefore $$\sigma_o = \frac{I(W_1\sigma_o)}{C\left(\frac{RX}{VN}\right)^\gamma [I(W)]^\gamma}$$

that is to say $$\sigma_o = K \frac{I(W\sigma_o)}{[I(W)]^\gamma},$$

where K is a constant $\sigma_o$ is dependent on the content of the salt dissolved in the liquid, and $I(W\sigma_o)$ and $I(W)$ are currents measured according to the method described above.

It is to be emphasized that during the measurement it is necessary to switch polarity of the current source to prevent electrochemical phenomena on the surface of the sensors.

Figure 7:
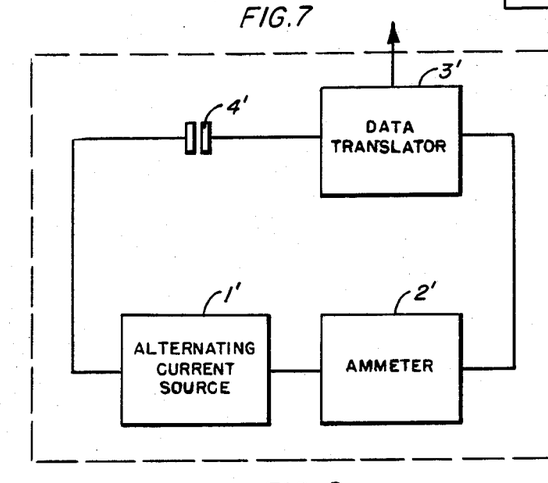
FIG. 7 is a schematic black illustration of a soil conductivity method and device, responsive to both the liquid content and salinity of, for example, a medium such as moist soil.

Straight conductivity testing provides the other required measurement, dependent upon both the content of liquid and the salinity thereof. With reference now to FIG. 7, there is shown and illustrated a conductivity tester which is responsive to change in both the liquid content and the salinity. 1' is an alternating current source. In series connection therewith is an ammeter 2' and data translator 3', all connected with a pair of spaced apart electrodes 4' in the porous medium to be tested. This device will hereinafter be referred to as a salinity unit.

Following is a description of several versions of devices according to the present invention which utilize different approaches and principles.

Figure 8:
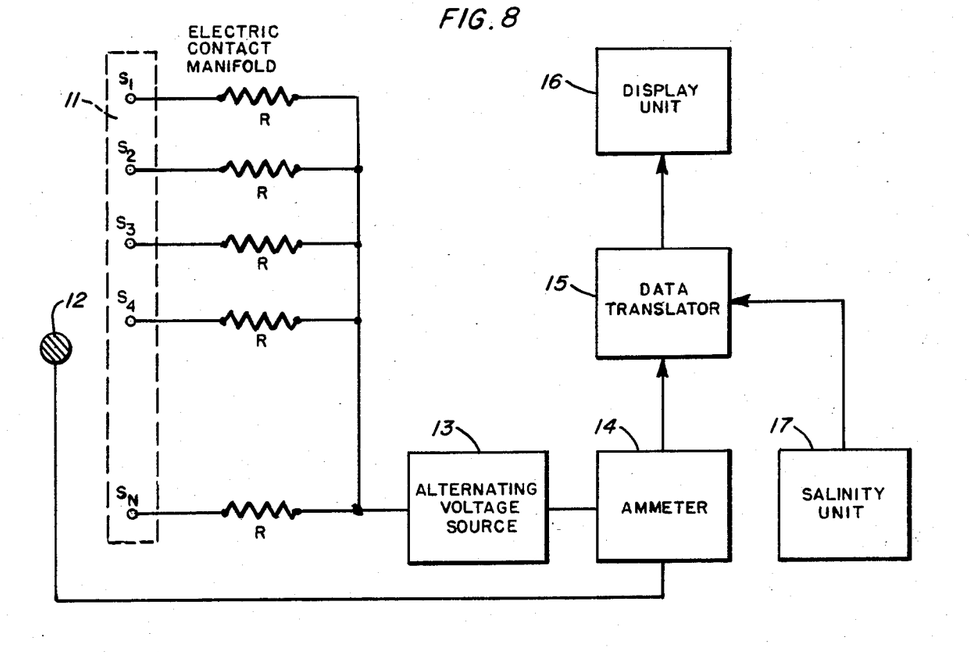
FIG. 8 is a schematic block illustration of another method and device responsive only to liquid content in a porous medium.

Version A (FIG. 8)
Description:

The instrument is constructed of an assemblage (11) of electrical point contacts ($S_1 \ldots S_n$) electrically connected to one terminal of N identical resistors of resistance R. The other terminals of the resistors are connected together to an alternating voltage source (13) whose other terminal is connected to an ammeter (14).

Another electrode (12) which can be either one, two or three dimensional is electrically connected to the other side of the ammeter (14). The meter output is read by the data translator (15). If there is a requirement for salinity measurement, the output of the salinity unit (17) is connected to another input of the data translator unit (15).

The output of the information translator (15) is transferred to the data display unit (16).

Operation

The group of contacts (11) and the additional electrode (12) are in contact with the medium under test when the point is not in physical contact with the liquid, in the medium. The distance between (11) and (12) is so determined that the electrical resistance of the measured medium between each contact point and the common electrode should be much higher ("infinite") than the resistance of each resistor. If there is physical contact between the contact points and the liquid in the medium, the electrical resistance measured between the contact point and the common electrode should be much smaller than the resistance of each resistor. Under these conditions, the current through the ammeter depends only on the probability of the existence of contact with the liquid as explained in the theory and, therefore, is a function of liquid content only.

Electrode (12) is two or three dimensional and made of metal, such as lead. The electrical contacts (11) are also made of metal. In the event that the contacts and electrode (12) are made of different metals, the alternating voltage source (13) must have a voltage significantly higher than the electrochemical potential difference which exists between two metals in the electrolytic medium.

It is necessary to prevent electrical contact between the point contacts or between the resistors (except the common connection point of the resistors).

The input to the data translator (15) is the current measured by the ammeter (14) and with the assistance of a theoretical equation or with an empirical calibration curve, it translates the current into moisture units. The translated data is connected from the translater (15) to the data display unit in either analogic or digital form.

If it is required to measure salinity, data translator (15), in addition to the operation described above, receives also the input obtained from the salinity unit (17) and translates the information into salinity units with the assistance of a theoretical equation or empirical calibration curve. This data too is passed on to the data display unit (16). In the instrument described above the contact assembly (11), the electrode (12) and the resistors (R) make up the moisture unit. The complete probe unit consists of the moisture unit together with the electrodes of the salinity unit (17) (as described hereinabove, see FIG. 7). The other units make up the display.

Limitations:

The use of the instrument is limited to porous media which do not conduct electricity when completely dry, and where the liquid in the medium is an electrolytic conductor (moist soil for example).

Version B (FIG. 9)
Description

Figure 9:
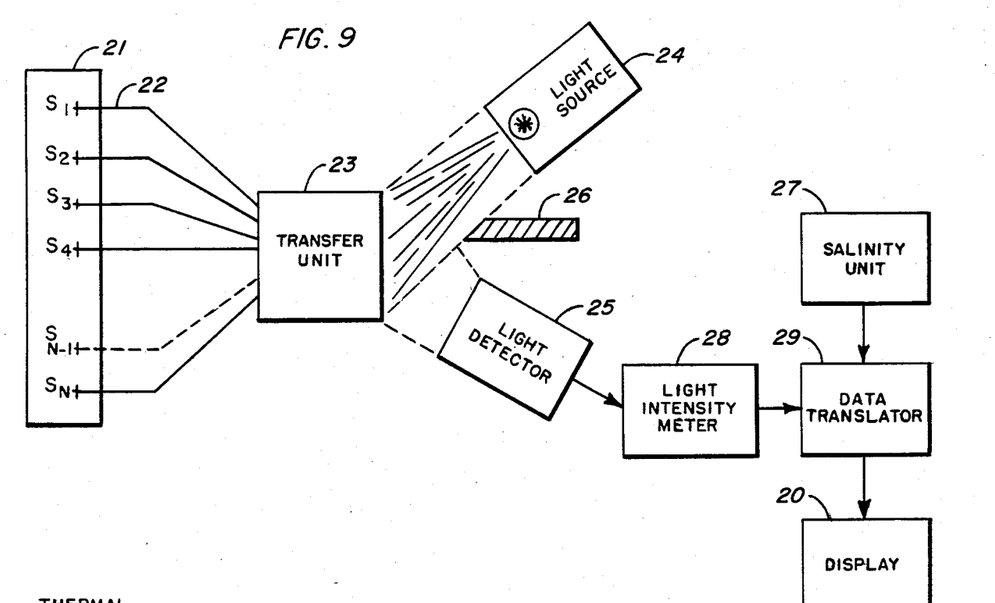
FIG. 9 is a schematic block illustration of yet another method and device responsive only to liquid content in a porous medium.

The instrument is constructed of (21) a group of optical point contacts $S_1 \ldots S_n$, which are mutually isolated optically but all of which are in optical contact with the medium under test. Each of the optical point contacts is optically connected to one end of a fiber-optic conductor (22) whose other end is connected to a transition unit (23). The transition unit (23) is irradiated by a light source (24) and simultaneously passes a light from the optical fibres to the light detector (25). A partition (26) is an optical isolator between the source (24) and the detector (25), thus, only the light from the fibres (22) reaches the detector. The output from the light detector serves as the input to the light intensity meter (28), and the output from this meter is connected to the data translator (29), which converts the light intensity into moisture units. This data is transmitted by either analogue or digital means to the data display unit (30). When it is desired to use the instrument for salinity measurements as well, the output of salinity unit (27) is connected to a second input of the data translator (29).

Operation

The group of optical contacts (21) is in optical contact with the measured medium. Light from light source (24) passes through the transfer unit (23) and the optical fibres (22) to the optical point contacts $S_1 \ldots S_N$. If the optical contact is in contact with the liquid, the light is dispersed in the liquid and is dissipated in the medium. When there is no contact with the liquid, the light is reflected from the end of the optical fibre, back through the fibre and transfer unit (23) to light detector (25). In this way the reflected light intensity collected by the detector is proportional to the number of optical point contacts in group (21), which are not in contact with the liquid in the medium. As explained above in the theory, the light intensity is dependent exclusively on the probability of the existence of non-existence of contact with the liquid. The reflected light intensity measured by the detector is a function, therefore, only of the liquid content.

Limitations

The use of the instrument is limited to porous media having a high optical absorption co-efficient in a dry medium, and where the liquid content is highly transparent. The index of refraction of the optical point contact has to be approximately equal to the index of refraction of the liquid, for example, damp coal.

Figure 10:
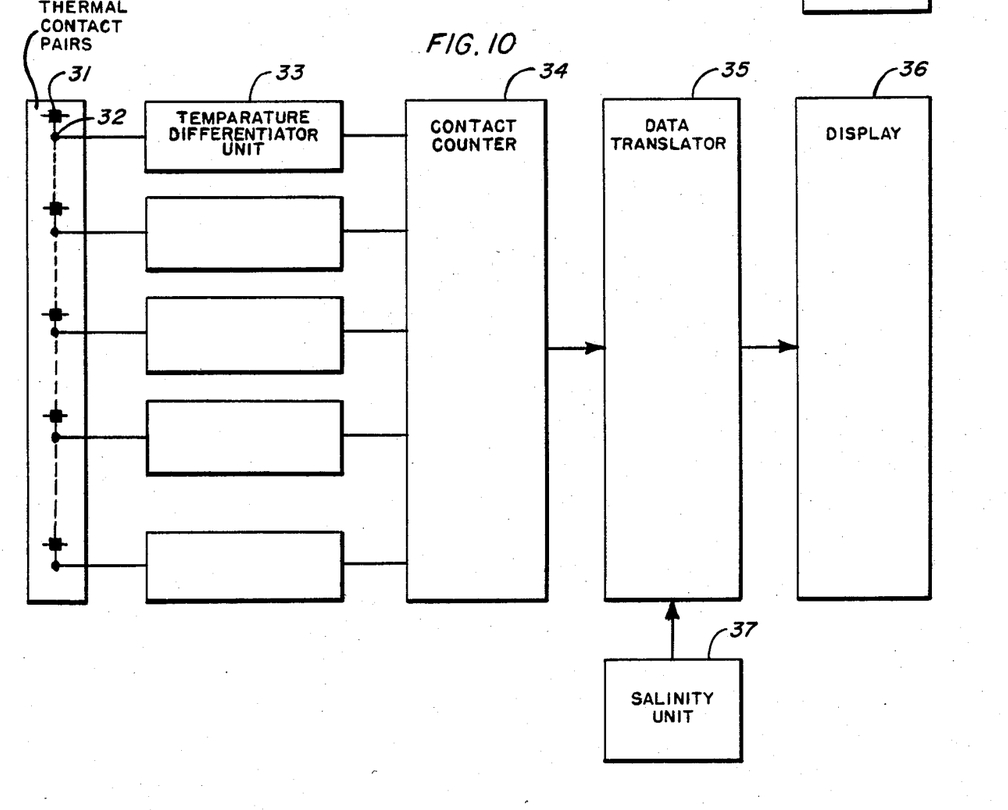
FIG. 10 is a schematic block illustration of still another method and device responsive only to liquid content in a porous medium.

Version C (FIG. 10)

Description

The instrument is constructed of a group (31) of thermal contact pairs ($S_1 \ldots S_N$) werein each pair is comprised of thermal point contact S(1), which is thermally connected to a heat source (such as, a point source heated wire) and another thermal point contact S(2) which is thermally connected to a heat measuring device (such as a thermocouple (32)). Each heat measuring device is connected to a group of temperature measuring units (33) where each unit distinguishes between the different temperature caused by the existence or non-existence of a physical contact through the liquid between the two contacts. Both contacts in each pair are thermally isolated between themselves so that the thermal contact between the two contacts can be created only by the liquid. The output from the temperature measuring units (33) is coupled to an input of contact counter (34) which counts the number of contact pairs which are in a thermal contact with the liquid. The output from the counter (34) is the input to the data translator (35) which translates the output from the counter (34) to the liquid content units through the use of an equation, algarithm or calibration curve. The output from the data translator (35) is connected by analogue or digital means to data display unit (36). When it is desired that the instrument be used for salinity measurements as well, the output of the salinity unit (37) is connected to a second input of the data translator (35).

Operation

The group of contacts (1) is in a thermal contact with the measured medium. The thermal point contact is connected to a heat source. The radiation from the contact passes through the medium to the second thermal point contact which is connected to heat measuring device. In the event that both contacts are in contact with liquid in the medium, the heat measuring device will show an increase in temperature which is typical of the heat-conducting characteristics of the liquid in the medium. When there is no simultaneous thermal connection between the contacts and the liquid, there will be less increase in temperature than in the first case, because of thermic dispersal of heat in the medium.

The group of temperature measuring units (33) is designed to distinguish between the different temperatures caused by the existence or non-existence of contact between each pair of contacts and the liquid. This distinction is obtained by selecting a minimum value of the temperature difference $\Delta T_o$, typical to the medium and liquid characteristics. The existence of contact as mentioned, will show temperature change $\Delta T > \Delta T_o$ which the non-existence of such contact will show a temperature change $\Delta T < \Delta T_o$. In this manner the number of contact pairs (1) which display temperature changes $\Delta T > \Delta T_o$ is dependent exclusively on liquid content. That is to say, that the contact counter (34) is counting the number of contacts in the group (1) which are in physical contact with the liquid in the medium. The number counted is proportional to the liquid content of the medium and depends only on the probability of the existence or non-existence of contact with the liquid as described above in the theory. Therefore, the number of contacts shown by the counter (34) is a functon of liquid content only.

Limitations

The use of the instrument is limited to porous mediums havng a coefficient of thermal conduction in the dry medium, smaller than the coefficient for the most medium. That is to say, that the dry medium has to be constructed of a highly thermally isolated material, as damp soil, for example.

Figure 11:
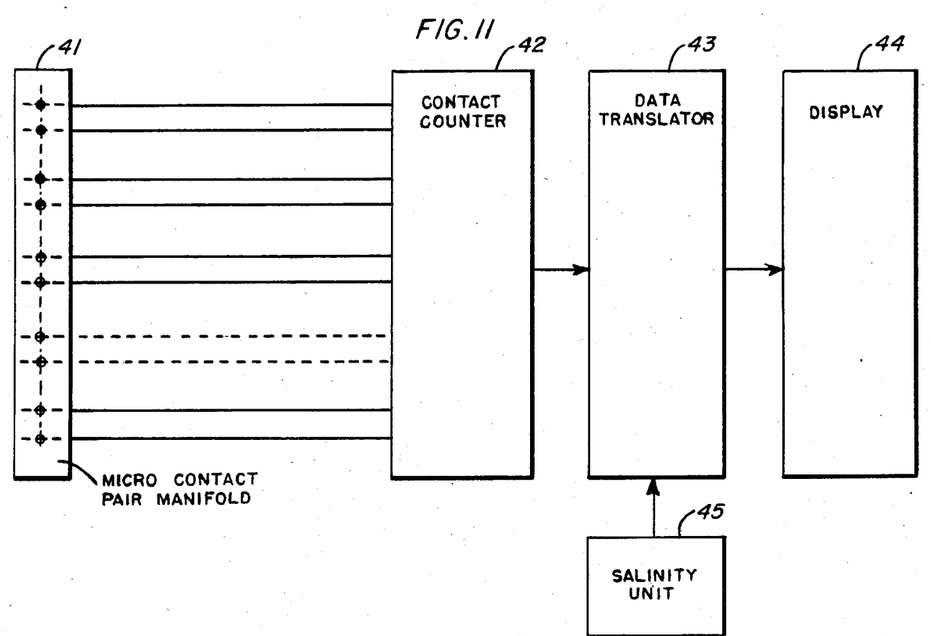
FIG. 11 is a schematic block illustration of yet still another method and device responsive only to liquid content in a porous medium.

Version D (FIG. 11)

Description

The instrument is constructed of (41) a group of electrical point contacts ($S_1 \ldots S_N$) which are mutually isolated electrically. Each pair is comprised of two point contacts which are very close one to the other and are in electrical contact with the medium. The contacts in each pair are also isolated between themselves.

Each pair is electrically connected to a contacts counter (42) which counts the number of pairs which are short-circuited by the liquid in the medium.

The output from the counter (42) is connected to the data translator (43) which, by means of an equation or calibration curve translates the number of shorted pairs to liquid-content units. The output from the data translator (43) is coupled to the input of the data display unit (44) by either an analogue or digital means. Where it is desired to use the instrument for salinity measurements as well, the output of the salinity unit (45) is connected to another input of the data translator (43).

Operation

The group of contacts (41) is in contact with the measured medium. Each pair of contacts is in one of the conditions, either shorted or open-circuited. The shorted condition is typical to the existence of conduction through the liquid between the two contacts, and the open-circuited condition is typical to the non-existence of such conduction.

In this manner, the number of contact pairs in the group (41) short circuited by the liquid in the medium is exclusively dependent on the probability of the existence of conduction between the contacts of each pair and the liquid in the medium. Therefore, as described in the theory, the number of contacts which are in a shorted condition and counted by the counter (42) is a function of liquid-content only.

Limitations

The use of the instrument is limited to porous mediums having electrical conductivity in a dry medium smaller than the electrical conductivity of the liquid, (that is to say, that the dry medium has to be an electrical non-conductor), for example, powders made of insulating material. The salinity unit for all the versions is as previously described.

Figure 12:
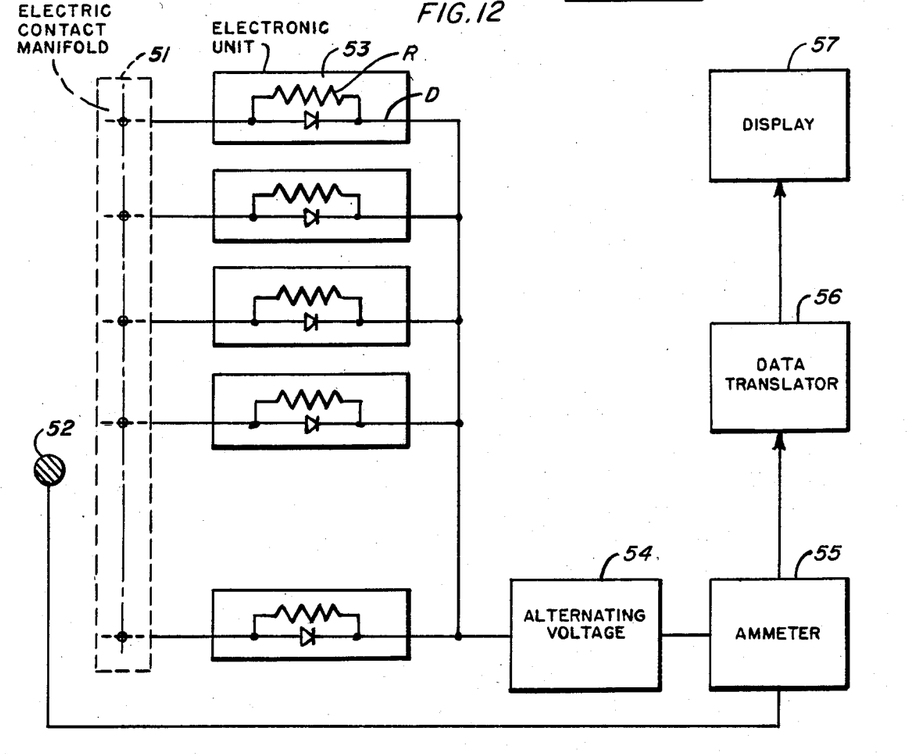
FIG. 12 is a schematic block illustration of a method and device responsive only to liquid content in a porous medium and also selectively responsive to both liquid content and salinity in the porous medium enabling independent output therefrom of either or both of liquid content and salinity.

Version E (FIG. 12)

Description

The instrument is constructed of a group (51) of electrical point contacts ($S_1 \ldots S_N$) which are electrically connected to one terminal of N similar electronic units (53). The electrical point contacts are mutually connected. Each of the electronic units is comprises of a resistor R and a doide D which are connected in parallel. The other terminal of each of these units (53) is connected together to a common point which is connected to an a-c voltage source (54). Another electrode which may be one, two or three dimensional (52) is electrically connected to one terminal of an ammeter (55) whose other terminal is connected to the other terminal of the a-c voltage source (54). The output obtained from the ammeter (55) is connected to the input of the data translator (56). The output of the translator is connected to the input of the data display unit (57). In this version of the instrument the moisture and salinity measurements are accomplished by the contacts (51) and the common electrode (52) and there is no necessity for a separate salinity unit.

Operation

The contacts (51) and the electrode (52) are in contact with the measured medium. The distance between (51) and (52), and the resistance of the resistor R is determined in the same manner as described in version A (FIG. 8) above.

The electronic units (53) operate as follows:

When a voltage drop between a contact (51) and the common electrode (52) causes the diode to be conductive, then the electric resistance of each electronic unit approaches zero. But when the voltage drop does not cause diode conduction, the electrical resistance of each electronic unit is R and this is similar to the operation of the instrument described in version A (FIG. 8).

In the case where the diodes are in a conductive condition, and the electrical resistance of each electronic unit is close to zero, the current measured by the ammeter (55) depends on the number of contacts which are in contact with the medium liquid, and on the electrical resistance of the medium. This current is, therefore, a function of both the liquid content in the medium and the salinity of the solution in the medium. It is possible, therefore, to measure with this instrument the two physical parameters described in the theory. That is to say, one is exclusively dependent only on the contents of the liquid in the medium, and the other parameter depends on both, liquid contents and the salinity of the solution in the medium. This is accomplished by selecting the electrical resistance value of the electronic units (53), either R or zero, dependent on the direction of the voltage drop between the contacts (51) and the common electrode (52). This is done automatically by means of the polarity change of the alternating voltage source (54).

The data translator (56) receives two kinds of information from the ammeter (55), one of the current which passes between the electrode (52) and the contacts (51) wherein the resistance of each electronic unit is R. The other kind of information is the current passes through between the electrode (52) and the contacts (51) wherein the resistance of each electronic unit is zero.

All other parameters as for example: kinds of metals, voltage magnitude, etc. are similar to that described in version A above.

The data translator (56) calculates the value of these two currents according to the equation or calibration curve, and translates them into salinity and liquid-content units. This information is transferred to the data display unit (57) by either analogue or digital means.

Limitations

The use of the instrument is limited to the mediums mentioned in version A (FIG. 8) above.

The salinity unit mentioned above in all versions, is as previously described.

After we have described, explained and proved above the characteristics of the method, the instrument and the operation, we hereby declare that our claims are:

1. A method for measuring liquid content of a porous medium such as soil, comprising the steps of:
   (a) placing a plurality of point contacts in contact with soil to be measured for liquid content;
   (b) applying a voltage to the point contacts;
   (c) inserting a predetermined electrical resistance between each of the point contacts and a source of the voltage applied to the point contacts;
   (d) arranging a common electrode in the soil to be measured for liquid content in spaced relation to the point contacts, and connecting the common electrode to the source of the voltage applied to the point contacts; and
   (e) determining the liquid content in the soil to be measured as a function of the number of the point contacts having electrical continuity with the common electrode through the soil to be measured for liquid content.

2. A method as set forth in claim 1, wherein the step of applying a voltage to the point contacts includes the step of alternatively changing the polarity of the voltage applied to the point contacts.

3. A method as set foth in claim 1, wherein the step of arranging a common electrode includes the step of determining the distance between the common electrode and the point contacts for the electrical resistance of the medium to be measured over the distance determined to be much higher than the resistance of each electrical resistance inserted between the point contacts and the source of voltage applied to the point contacts.

4. A method as set forth in claim 3, wherein the step of applying a voltage to the point contacts includes the step of alternatively changing the polarity the voltage applied to the point contacts.

5. A method as set foth in claim 4, wherein the step of changing polarity of the voltage includes the step of supplying an alternating voltage.

* * * * *